United States Patent [19]
Lee et al.

[11] Patent Number: 5,180,570
[45] Date of Patent: Jan. 19, 1993

[54] INTEGRATED PROCESS FOR MAKING METHANOL AND AMMONIA

[76] Inventors: Jing M. Lee, 11602 Blair Meadow, Stafford, Tex. 77477; Joseph R. LeBlanc, 4439 Cherry Oak La., Houston, Tex. 77088

[21] Appl. No.: 824,954

[22] Filed: Jan. 23, 1992

[51] Int. Cl.$^5$ .......................... C01C 1/04; C07C 27/06
[52] U.S. Cl. .................................... 423/359; 422/148; 422/190; 518/703; 518/704
[58] Field of Search .................. 423/359; 518/703, 704

[56] References Cited

U.S. PATENT DOCUMENTS

| | | | |
|---|---|---|---|
| 3,404,957 | 10/1968 | Blaskowski | 423/359 |
| 3,598,527 | 8/1971 | Quartulli et al. | 23/199 |
| 4,315,900 | 2/1982 | Nozawa et al. | 423/359 |
| 4,367,206 | 1/1983 | Pinto | 423/359 |
| 4,443,560 | 4/1984 | Le Blanc, Jr. et al. | 518/704 |
| 4,810,417 | 3/1989 | Diemer et al. | 252/373 |
| 4,886,651 | 12/1989 | Patel et al. | 423/359 |
| 4,888,130 | 12/1989 | Banquy | 252/373 |

*Primary Examiner*—Wayne Langel
*Attorney, Agent, or Firm*—The M. W. Kellogg Company

[57] ABSTRACT

An integrated process for making methanol and ammonia from a hydrocarbon feed stock and air is disclosed. An air separation unit is used to produce substantially pure oxygen and nitrogen gas streams. The oxygen gas is used in the secondary reformer to increase the operating pressure of the reformers so that compression to methanol synthesis pressure may be done by a single stage compressor. The nitrogen gas is used to remove carbon oxides impurities from a ammonia synthesis feed stream in a nitrogen wash unit in addition to supplying the nitrogen reactant in the ammonia synthesis gas. Use of nitrogen wash obviates the need for steam shift and methanation reactions used in prior art processes.

6 Claims, 1 Drawing Sheet

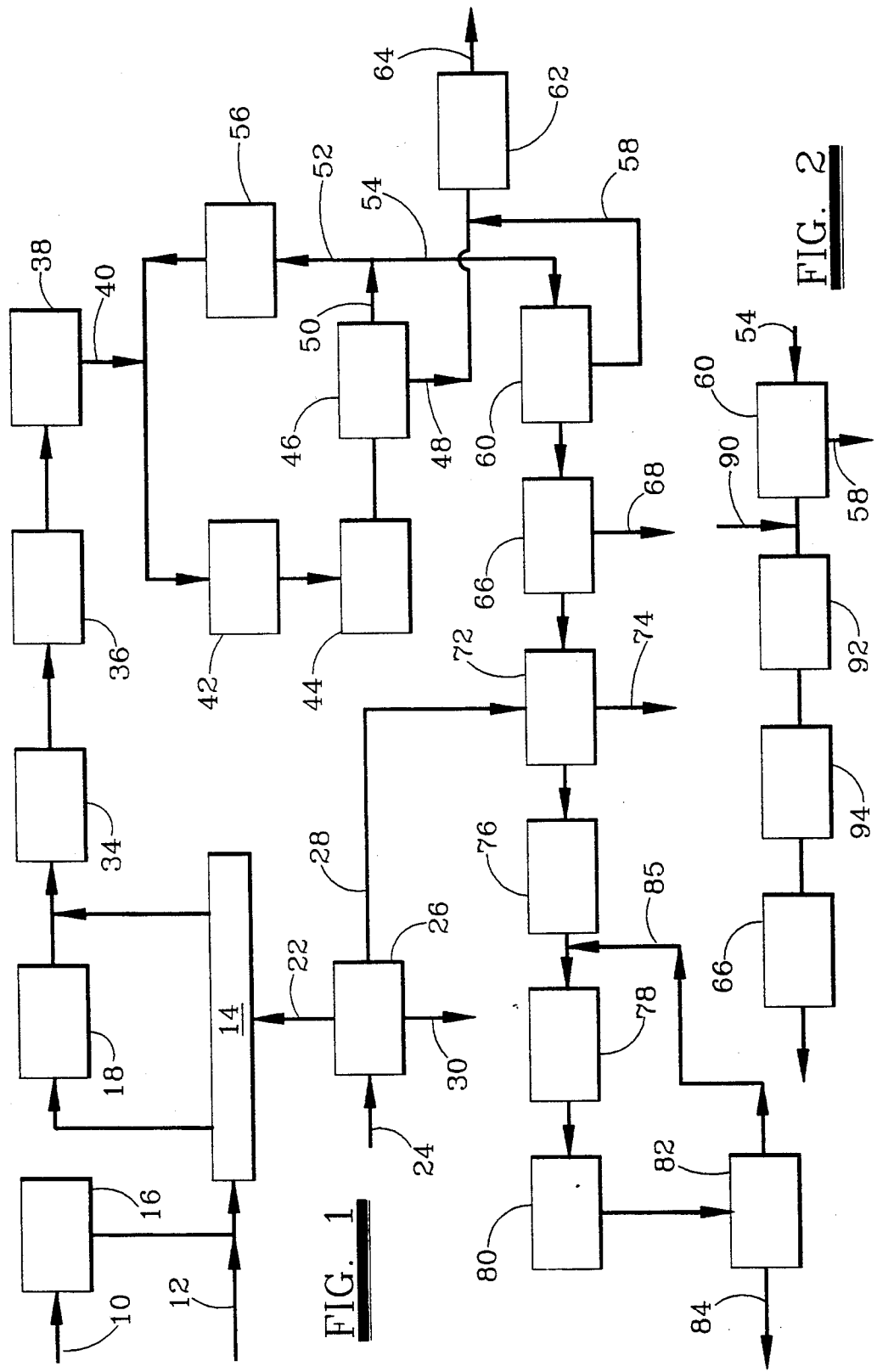

INTEGRATED PROCESS FOR MAKING METHANOL AND AMMONIA

FIELD OF THE INVENTION

The present invention relates to an integrated process for making methanol and ammonia, more specifically, an integrated methanol/ammonia process wherein an air separation plant provides a pure oxygen stream for a secondary reforming step, and a pure nitrogen stream for absorbing residual carbon oxides and as a reactant in an ammonia synthesis step.

BACKGROUND OF THE INVENTION

Methanol is generally made from a mostly methane hydrocarbon feed by first catalytically oxidizing the feed at high temperature to produce a synthesis gas. This oxidation reaction is known in the art as hydrocarbon reforming. Reforming is usually conducted using steam as an oxidant, however, steam reforming is frequently supplemented by secondary reforming using oxygen or an oxygen-containing gas. Methanol is then catalytically synthesized from the direct combination of the hydrogen and carbon oxides in the synthesis gas. Because of a low molecular carbon to hydrogen ratio for saturated hydrocarbon feeds and a minimum required steam rate, hydrogen is generally present in large stoichiometric excess in the synthesis gas. However, a large hydrogen excess is undesirable for methanol synthesis and much effort has been expended to balance the stoichiometric composition of the synthesis gas. U.S. Pat. No. 4,888,130 to Banquy, for example, discloses a process for producing a synthesis gas suitable for methanol production or other synthesis requiring a low $H_2/CO$ ratio. The feedstock is divided into two fractions and the first fraction undergoes primary steam reforming. The gas effluent is combined with the second feedstock fraction and undergoes secondary reforming with an oxygen-containing gas.

Alternatively, the significant hydrogen-rich stream from methanol production is available for further use such as, for example, ammonia production. U.S. Pat. No. 3,598,527 to Quartulli et al., for example, discloses a process for the production of methanol and ammonia. This process involves operating sequentially and in series a high pressure hydrocarbon reforming zone, a low pressure methanol synthesis zone, a water shift conversion zone, a carbon dioxide removal zone, and an ammonia synthesis zone. The reforming zone includes air reforming following steam reforming to provide nitrogen sufficient to satisfy the requirement for ammonia production. Carbon dioxide removal includes a regenerative $CO_2$ absorption system and methanation to eliminate residual carbon oxides.

U.S. Pat. No. 4,315,900 to Nozawa et al. discloses an integrated process for the production of methanol and ammonia wherein secondary steam and air reforming to produce an ammonia synthesis gas follows the methanol synthesis. A methanol synthesis gas is produced by primary steam reforming of a hydrocarbon feed. Shift converters are used to reduce CO content of the ammonia synthesis gas and $CO_2$ removal is effected by absorption and methanation prior to ammonia synthesis.

U.S. Pat. No. 4,367,206 to Pinto discloses a method for producing methanol and ammonia by generating a nitrogen containing synthesis gas, reacting the carbon oxides and hydrogen incompletely to methanol and passing the unreacted gas to ammonia synthesis. The process is characterized by catalytic methanol synthesis in a first steam-free stage and then in a second stage in the presence of sufficient steam to convert substantially all the unreacted CO to $CO_2$. Methanol can be taken from the second synthesis stage as a product or vaporized and recycled as a source of steam for this stage. Recycling concentrates the methanol inlet concentration to the catalyst and suppresses the net formation of methanol for increasing subsequent ammonia production.

U.S. Pat. No. 4,810,417 to Diemer et al. discloses a process for the simultaneous production of methanol synthesis gas and ammonia synthesis gas from crude coal gasification products.

SUMMARY OF THE INVENTION

An integrated methanol and ammonia synthesis process of the present invention uses a substantially pure oxygen stream and a substantially pure nitrogen stream from an air separation unit to reduce capital and energy requirements and enhance production flexibility. By shifting reforming load to a secondary reformer utilizing substantially pure oxygen, the primary reformer is run at a milder temperature and higher pressure. As a result, the methanol synthesis makeup gas is more readily compressed to a methanol synthesis loop pressure, for example, in a single compression stage. In addition, a higher rate of hydrocarbon conversion is obtained in the reforming step to reduce methane concentration in the makeup gas for low-inerts operation of the methanol synthesis reactor. A pure nitrogen stream wash removes carbon oxides and provides nitrogen to form an ammonia synthesis gas. The nitrogen wash obviates the need for CO to $CO_2$ shift reaction steps and a carbon oxide to $CH_4$ methanation step typically present in the prior art although a shift reaction step can be used if desired to increase ammonia production.

In one embodiment, the present invention provides an integrated process for making methanol and ammonia. In a first step, air is separated into a substantially pure nitrogen stream and a substantially pure oxygen stream. In another step, a desulfurized hydrocarbon feed with steam at a molar ratio of steam to carbon of from about 2.5 to about 3.5 is reformed in an indirectly heated primary reforming zone at a pressure of from about 2.7 MPa(g) (400 psig) to about 5.2 MPa(g) (750 psig), preferably from about 3.1 MPa(g) (450 psig) to about 4.1 MPa(g) (600 psig), and an exit temperature of from about 750° C. (1400° F.) to about 900° C. (1650° F.), preferably from about 800° C. (1450° F.) to about 850° C. (1550° F.), to form a partially reformed hydrocarbon stream. The partially reformed stream is reformed in another step with the oxygen stream in an adiabatic secondary reforming zone at a pressure of from about 2.7 MPa(g) to about 5.2 MPa(g), preferably from about 3.1 MPa(g) to about 4.1 MPa(g), and an exit temperature of from about 900° C. to about 1050° C., preferably from about 950° C. to about 1000° C., to form a methanol synthesis gas makeup stream containing less than 3 mole percent methane, preferably less than 1 mole percent. In another step, a methanol synthesis gas feed stream, including the methanol synthesis gas makeup stream, is passed to a methanol synthesis zone operated at a pressure of from about 6.2 MPa(g) (900 psig) to about 10.3 MPa(g) (1500 psig), preferably from about 7.6 MPa(g) (1100 psig) to about 9.0 MPa(g) (1300 psig). Another step includes separating a recycle gas stream from methanol produced in the methanol synthesis zone. The crude methanol stream is removed for purification. A first portion of the recycle gas stream is recycled to the methanol synthesis gas feed passage step. A second portion of the recycle gas stream is removed as a purge gas stream. The purge gas stream is treated for $CO_2$ removal, washed with nitrogen to remove remaining carbon oxides and methane and mixed with a stoichiometric proportion of the nitrogen to produce an ammonia synthesis gas stream. The ammonia synthesis gas is reacted in an ammonia synthesis zone at a pressure of from about 8.3 MPa(g) (1200 psig) to about 17.2 MPa(g) (2500 psig), preferably from about 12.4 MPa(g) (1800 psig) to about 14.5 MPa(g) (2100 psig), to produce ammonia which is recovered.

In a preferred embodiment, the methanol synthesis gas is compressed to the methanol synthesis zone pressure using single-stage compression and is essentially free of inert gases. A specific duty of the secondary reforming zone with respect to the hydrocarbon feed conversion preferably comprises from about 15 to about 40 percent of the total combined duty of the primary and secondary reforming zones, more preferably from about 20 to about 30 percent.

In another embodiment, the present invention provides an integrated plant for the production of methanol and ammonia. The plant comprises as a first unit an air separation unit for forming substantially pure streams of oxygen and nitrogen from air. The plant has a primary reformer for partially reforming a desulfurized hydrocarbon feed with steam at a molar ratio of steam to carbon of from about 2.5 to about 3.5, at a pressure of from about 2.7 MPa(g) to about 5.2 MPa(g) and an exit temperature of from about 750° C. to about 900° C. to give a partially reformed hydrocarbon stream. The plant also has a secondary reformer for adiabatically reforming the partially reformed stream with the oxygen stream, at a pressure of from about 2.7 MPa(g) to about 5.2 MPa(g) and an exit temperature of from about 900° C. to about 1050° C. to form a methanol synthesis gas makeup stream containing less than about 3 mole percent methane. A methanol synthesis reactor is adapted to catalytically produce methanol at a pressure of from about 6.2 MPa(g) to about 10.3 MPa(g) from a methanol synthesis gas including the makeup stream and at least a first portion of a recycle gas stream separated from the methanol, such that the methanol synthesis gas preferably comprises less than about 10 mole percent of inerts. A carbon dioxide removal unit is adapted to remove carbon dioxide from a purge gas stream removed as a second portion of the recycle gas stream. The plant has a nitrogen wash unit for removing carbon monoxide, residual methane and residual carbon dioxide from the purge gas stream, and mixes nitrogen with the purge gas to form an ammonia synthesis gas. An ammonia synthesis reactor is adapted to form ammonia from the ammonia synthesis gas at a pressure of from about 8.3 MPa(g) to about 17.2 MPa(g).

BRIEF DESCRIPTION OF THE DRAWINGS

FIG. 1 illustrates a schematic flowsheet of one embodiment of the integrated methanol and ammonia process of the present invention.

FIG. 2 illustrates a partial schematic flowsheet of another embodiment of the integrated methanol and ammonia process of the present invention showing use of an optional shift converter.

DETAILED DESCRIPTION OF THE PREFERRED EMBODIMENTS

An integrated methanol and ammonia plant of the present invention utilizing substantially pure oxygen and nitrogen streams separated from air has reduced energy requirements and capital costs and enhanced production flexibility. The pure oxygen stream is used to enhance reformer operating efficiency for making a methanol synthesis gas. The pure nitrogen stream is used to remove undesirable carbon monoxide, carbon dioxide and methane from a methanol synthesis purge stream, as well as to provide nitrogen for ammonia synthesis.

Referring to FIG. 1, a gaseous hydrocarbon feed under pressure is introduced through line 10 and heated to a temperature on the order of 370° C. (700° F.) by a preheater 14. The hydrocarbon feed is typically methane or natural gas, but other hydrocarbon feeds are known in the art. Methane is referred to hereinbelow for the sake of brevity and clarity with the understanding that the invention is not limited thereto. If the feed contains sulfur, the heated hydrocarbon gas can be directed to a sulfur removal unit 16 comprising, for example, a catalytic hydrotreater to hydrogenate sulfur to hydrogen sulfides and an absorber containing Co-Mo catalyst, zinc oxide, and the like for absorbing the hydrogenated sulfides. The feed should be free of sulfur components to avoid poisoning the various catalysts used for reforming, methanol synthesis and ammonia synthesis.

The desulfurized hydrocarbon effluent gas is mixed with steam from line 12 and heated by the preheater 14 to an inlet temperature of a primary reformer 18 on the order of 620° C. (1150° F.). A molar ratio of steam to carbon atomic weight of the feed gas is from about 2.5 to about 3.5 to 1. Much of the methane is decomposed in the primary reformer 18 to $H_2$, CO and $CO_2$ to produce a methanol synthesis gas. The primary reformer 18 is operated at a pressure of from about 2.7 MPa(g) to about 5.2 MPa(g), preferably from about 3.1 MPa(g) to about 4.1 MPa(g) and a temperature of from about 750° C. to about 900° C., preferably from about 800° C. to about 850° C. The primary reformer 18 contains a conventional catalyst, e.g. nickel, and is heated conventionally, e.g. in the radiant heating chamber in a fired furnace.

A secondary reformer 34 is used to perform additional reforming duty. The hot effluent gas from the primary reformer 18 containing unreacted methane and any other hydrocarbons is preferably mixed with substantially pure oxygen gas and heated by the preheater 14 to an inlet temperature of the secondary reformer 34 on the order of 450° C. (842° F.). The oxygen gas is produced from an air separation unit 26 and introduced in line 22. In the secondary reformer 34, most of the remaining unreformed hydrocarbons (methane) are reacted using oxygen gas as the oxidizer. Following secondary reforming, unreacted methane in the methanol synthesis gas is less than about 3 mole percent, preferably less than 1.0 mole percent.

The secondary reformer 34 has an operating pressure of from about 2.7 MPa(g) to about 5.2 MPa(g), preferably from about 3.1 MPa(g) to about 4.1 MPa(g), and an operating temperature of from about 900° C. to about 1050° C., preferably from 950° C. to about 1000° C. With respect to hydrocarbon feed conversion to reformed products, a specific duty of the secondary reformer 34 comprises from about 15 to about 40 percent of the total combined primary and secondary reforming duty, preferably from about 20 to about 30 percent of the combined reforming duty. Stated differently, the primary reformer 18 does from about 60 to about 85 percent of the methane reforming, preferably, from about 70 to about 80 percent.

The methanol synthesis gas from the secondary reformer 34 is typically directed to waste heat recovery equipment 36 wherein sensible heat of the gas is used to perform a variety of heating duty such as heating boiler feed water, vaporizing crude methanol, and the like. Heat transfer against process and utility streams in a manner well known in the art preferably cools the synthesis gas to a temperature of about 38° C. (100° F.). Steam condensation and removal is effected in a separation vessel or other conventional equipment. The cooled, dehydrated methanol synthesis gas is compressed by a makeup compressor 38 to a methanol synthesis pressure of from about 6.2 MPa(g) to about 10.3 MPa(g).

The compressed methanol synthesis gas is introduced in line 40 (methanol synthesis makeup), combined with recycle methanol synthesis gas and heated by heat exchange against hot methanol synthesis effluent. The combined methanol synthesis gas is directed to the methanol synthesis unit 42, wherein methanol is produced in the presence of a conventional copper catalyst, for example, at a temperature of from about 210° C. (410° F.) to about 270° C. (518° F.). Since conversion to methanol is incomplete, an effluent from the methanol synthesis unit 42 containing methanol and unreacted methanol synthesis gas is passed into cooling equipment 44 to effect condensation of liquids which are withdrawn in line 48 as crude methanol and separated from the unreacted methanol synthesis gas in line 50. The crude methanol is directed to conventional methanol purification equipment 62 where impurities are removed by distillation, for example. A refined methanol stream is recovered through line 64.

A first portion of the unreacted methanol synthesis gas in line 50 is, as previously mentioned, recycled to the methanol synthesis equipment 42. The recycle methanol synthesis gas 52 is compressed to compensate for pressure losses in the methanol synthesis unit 42, and then combined with the makeup gas for reuse in the methanol unit 42 as previously mentioned. A second portion of the unreacted methanol synthesis gas is withdrawn as a purge gas stream in line 54 in order to avoid accumulation of methane, nitrogen, and other inert substances, as well as excess hydrogen. The purge gas typically comprises 70–90 mole percent $H_2$, 1–7 mole percent CO, 1–7 mole percent $CO_2$, 0.5–5 mole percent $CH_4$, 0.5–5 mole percent methanol and 0–6 mole percent $N_2$. The hydrogen in the purge gas stream is used as a raw material for the ammonia synthesis.

The purge gas is fed through line 54 to a conventional methanol wash unit 60 Such equipment can comprise, for example, a water scrubbing column. Methanol removed from the purge gas is withdrawn through a line 58 for purification.

The effluent gas from the methanol wash unit 60 is directed to a carbon dioxide removal unit 66 comprising, for example, an absorption column employing an aqueous amine absorbent such as monoethanolamine and a stripping column for regenerating the amine absorbent. Carbon dioxide removed from the purge gas is withdrawn through a line 68.

The effluent gas of the amine absorption column in the carbon dioxide removal unit 66 is cooled in a condenser against a refrigerant to a temperature on the order of 10° C. to remove water by condensation. A molecular sieve bed is typically used to absorb residual $CO_2$ and $H_2O$. The dehydrated gas is cooled in a cold box exchanger to effect cooling to a temperature on the order of −180° C. (−290° F.) and then fed to a nitrogen wash unit 72 to remove carbon monoxide and other residual components which are either inert or detrimental to the ammonia synthesis catalyst. The nitrogen wash unit 72 comprises a cryogenic fractionation tower operating at an average temperature of −184° C. (−300° F.), wherein liquid nitrogen greater than about 99.5 mole percent purity is used to absorb CO and $CH_4$ which are withdrawn as a bottoms liquid by line 74. The nitrogen is produced in the air separation unit 26 and is supplied through line 28 at a rate sufficient to produce an ammonia synthesis gas leaving the wash unit 72 as an overhead vapor product having a stoichiometric proportion of nitrogen to hydrogen.

The ammonia synthesis gas leaving the nitrogen wash 72 is compressed to a pressure of an ammonia synthesis unit 80, combined with an ammonia synthesis recycle gas and heated by heat transfer against hot ammonia synthesis effluent. The combined ammonia synthesis gas, heated and compressed, is passed through the ammonia synthesis unit so where in the presence of an iron catalyst, ammonia is produced. The ammonia synthesis unit 80 is operated at a temperature of from about 230° C. (450° F.) to about 480° C. (900° F.) and at a pressure of from about 8.3 MPa(g) to about 17.2 MPa(g).

The hot effluent gas leaving the ammonia synthesis unit 80 comprising ammonia vapor and unreacted gas is passed through a heat recovery system such as steam superheater, boiler and cross exchanger to heat the incoming gas as mentioned above to recover waste heat and water-cooled to near ambient temperature. In a refrigeration unit 82, the ammonia effluent gas is further cooled to effect condensation of the ammonia vapor and separation from the unreacted gas. The recycle gas 85 separated from the liquid ammonia is compressed to compensate for pressure losses and combined with the ammonia synthesis makeup gas for reuse in the ammonia synthesis unit 80. Liquid ammonia is recovered through line 84.

The air separation plant 26 utilizes conventional equipment and techniques, such as liquefaction of air introduced in line 24 followed by cryogenic distillation, to produce oxygen gas in line 22, nitrogen gas in line 26, and primarily liquid argon in line 30.

Referring to FIG. 2, production of ammonia can be boosted when the carbon monoxide component of the methanol synthesis purge gas in line 54 is catalytically reacted with steam in a shift reaction. Following the methanol wash 60, the purge effluent gas is mixed with steam from line 90 at a proportion of about 2 to about 3 moles steam per mole carbon monoxide, heated to a temperature on the order of 210° C. (410° F.), and passed to a shift convertor 92 in the presence of a shift catalyst, the carbon monoxide is converted to carbon dioxide and hydrogen for ammonia synthesis. The hot effluent from the shift convertor 92 is then passed to waste heat recovery equipment 94 to cool the purge gas prior to carbon dioxide removal.

Focusing first on the methanol synthesis section of the present integrated process, several advantages over the prior art are evident. Shifting a portion of the reforming duty to a secondary reformer reduces the size and operating temperature required of the primary reformer and permits the increase of reforming operating pressure. Higher reforming operating pressure reduces the amount of compression required for methanol synthesis. Secondary reforming uses oxygen gas instead of air to substantially eliminate inert nitrogen buildup in the methanol synthesis loop. A reduction in inerts such as nitrogen (or methane) in methanol synthesis gas enhances conversion in the methanol reactor and decreases compression costs. Additional benefits from using oxygen gas in the secondary reformer are increased overall reforming conversion (hence lower inert methane in the methanol synthesis loop) and lower catalyst volumes needed. These process innovations result in significant energy and capital savings.

The ammonia synthesis portion of the integrated process also reduces energy and capital costs. Pure nitrogen gas is available for removal of carbon oxides. The nitrogen wash unit replaces high temperature shift reaction and methanation units typically used in the prior art. In addition, the present integrated process has flexibility to adjust methanol and ammonia production to market needs. For example, the methanol synthesis recycle gas flowrate can be reduced and the purge gas correspondingly increased to lower methanol production rate and increase ammonia production rate.

EXAMPLE 1 AND COMPARATIVE EXAMPLE 1

An integrated methanol and ammonia synthesis process of the present invention (Example 1, FIG. 1) is used to produce methanol and ammonia. The design basis is shown in Table 1. This plant is then compared to a plant also based on the Table 1 criteria, except that the methanol and ammonia units are not integrated other than to supply the methanol synthesis purge stream to the ammonia plant for ammonia synthesis (Comparative Example 1). In the comparison plant, secondary reforming is not used. From the resulting material balance, heat balance and process conditions for each design as seen in Table 2, a comparison of energy and capital costs can be made (Tables 3 and 4).

TABLE 1

| Design Criteria | |
|---|---|
| Methanol Synthesis Unit | Ammonia Synthesis Unit |
| Natural gas feed and fuel | Air separation unit for producing $N_2$ |
| Seawater desalination | Feed from methanol synthesis purge gas |
| Seawater cooling | |
| 2270 metric tons per day (MTD) methanol capacity | |
| No feed compressor | |
| In plant power generation | |

TABLE 2

Comparison of Process Conditions

| (2270 MTD methanol synthesis) | Comp. Ex. 1 | Ex. 1 |
|---|---|---|
| Reformer feed rate (kg mole/hr) | 3798.8 | 3448.6 |
| Reformer steam/carbon ratio | 3.0 | 3.0 |
| Reformer duty (kw) | 248,102 | 183,460 |
| Reformer exit temperature (°C.) | 860 | 832 |
| Reformer pressure (MPa(g)) | 1.93 | 3.45 |
| Reformer exit methane concentration (%) | 4.45 | 10.63 |
| Oxygen feed rate to secondary reformer (kg mole/hr) | — | 776.7 |
| Oxygen/steam inlet temperature (°C.) | — | 427 |
| Methanol makeup gas flowrate (kg mole/hr) | 14,883.5 | 13,250 |
| Methanol makeup gas methane concentration (%) | 4.45 | 0.93 |
| Methanol synthesis gas flowrate (kg mole/hr) | 71,844.6 | 58,120.4 |
| Methanol synthesis reaction beds | 4 | 4 |
| Methanol synthesis conversion (%) | 5.0 | 6.0 |
| Methanol synthesis inerts concentration (%) | 13.14 | 4.0 |
| Methanol synthesis catalyst volume (m³) | 165.5 | 104.2 |
| Methanol synthesis gas makeup compression power (kw) | 27,548 | 16,820 |
| Methanol synthesis gas recycle compression power (kw) | 2966 | 2332 |
| Air compression power (kw) | * | 4406 |
| Oxygen compression power (kw) | — | 2383 |
| Total methanol synthesis compression power (kw) | 30,514 | 26,041 |

*See Table 3

TABLE 3

Energy Consumption Comparison

| | Comp. Ex. 1 | Ex. 1 |
|---|---|---|
| Methanol Synthesis (2270 MTD) | | |
| Feed[a] (kw) | 861,973 | 799,878 |
| Net Fuel[b] (kw) | 312,266 | 279,120 |
| Ammonia plant credit (kw) | (275,970) | (224,082) |
| Total (kw) | 898,269 | 854,916 |
| kw per MTD methanol[c] | 9,497 | 9,039 |
| Ammonia Synthesis | | |
| Ammonia production (MTD) | 949 | 762 |
| Net feed (kw)[a,d] | 241,093 | 194,767 |
| Air compression (kw) | 13,447 | 10,826 |
| $N_2$ compression (kw) | 19,814 | 15,930 |
| Misc. power (kw) | 29,220 | 23,488 |
| Heat Recovery Credit (kw) | 27,593 | 20,860 |
| kw per MTD ammonia[c] | 6,980 | 7,060 |

[a]Low heating value (LHV) basis
[b]Adjusted to supply energy to the ammonia plant
[c]All in energy requirement
[d]After credit for reject gas fuel value Major areas of capital savings o the present invention over the methanol plant and ammonia plant taken individually are seen in lower reformer cost, lower compressor cost and lower methanol synthesis catalyst cost. These savings are offset somewhat by the cost of the secondary reformer and catalyst and additional air separation plant costs. The integrated plant of the present invention, however, has a significant overall net estimated capital savings as shown in Table 4.

TABLE 4

Capital Cost Differential (1989 U.S. Dollars)

| | Differential[a] | Cost (MM $) |
|---|---|---|
| Primary reformer[b] (kw/hr) | −69,265 | −5.44 |
| Methanol synthesis[c] compressor (kw) | −4473 | −1.12 |
| Methanol synthesis unit and catalyst[d] (m³) | −61.24 | −3.0 |
| Secondary reformer and catalyst[e] (m³) | +22.65 | +0.75 |
| Air separation unit | — | +2.0 |
| Misc | — | +0.3 |
| Net | — | −6.51 |

[a]savings made by the present invention represented by minus sign
[b]basis for reformer capital cost is $78.5/kw
[c]basis for compressor capital cost is $250/kw
[d]basis for reactor/catalyst cost is $49,000/m³ catalyst required
[e]basis for reformer/catalyst cost is $33,000/m³ catalyst required The foregoing description of the invention is illustrative and explanatory thereof. Various changes in the materials, apparatus, and particular parts employed will occur to those skilled in the art. It is intended that all such variations within the scope and spirit of the appended claims be embraced thereby.

What is claimed is:

1. An integrated process for making methanol and ammonia, comprising the steps of:

separating air into a substantially pure nitrogen stream and a substantially pure oxygen stream;

reforming a desulfurized hydrocarbon feed with steam at a molar ratio of steam to carbon of from about 2.5 to about 3.5 in a primary reforming zone, at a pressure of from about 2.7 MPa(g) to about 5.2 MPa(g) and at an exit temperature of from about 750° C. to about 900° C., to form a partially reformed hydrocarbon stream;

reforming said partially reformed stream with said oxygen stream and steam in an adiabatic secondary reforming zone, at a pressure of from about 2.7 MPa(g) to about 5.2 MPa(g) and at an exit temperature of from about 900° C. to about 1050° C., to form a methanol synthesis gas makeup stream containing less than about 3 mole percent methane;

passing a methanol synthesis gas feed including said makeup stream to a methanol synthesis zone operated at a pressure of from about 6.2 MPa(g) to about 10.3 MPa(g);

separating a recycle gas stream from methanol produced in the methanol synthesis zone to form a crude methanol stream;

recycling a first portion of said recycle gas stream to said methanol synthesis zone in said methanol synthesis gas feed passage step;

removing a second purge portion of said recycle gas stream as a purge gas stream;

treating said purge gas stream for $CO_2$ removal;

washing said purge gas stream with nitrogen from said nitrogen stream to remove residual carbon oxides and methane, wherein said purge portion is mixed with a stoichiometric proportion of said nitrogen to produce an ammonia synthesis gas stream;

reacting said ammonia synthesis gas in an ammonia synthesis zone at a pressure of from about 8.3 MPa(g) to about 17.2 MPa(g) to form ammonia;

recovering said ammonia from the ammonia synthesis zone.

2. The process of claim 1, comprising single-stage compression of said methanol synthesis gas to said methanol synthesis zone pressure.

3. The process of claim 1, wherein the methanol synthesis makeup stream is essentially free of inert gases.

4. The process of claim 1, wherein a specific duty of said secondary reforming zone with respect to said hydrocarbon feed conversion comprises from about 15 to about 40 percent of the total combined reforming duty of said primary and secondary reforming zones.

5. The process of claim 1, wherein a specific duty of said secondary reforming zone with respect to said hydrocarbon feed conversion comprises from about 20 to about 30 percent of a combined reforming duty.

6. The process of claim 1, further comprising the step of subjecting said purge gas to shift conversion prior to said carbon dioxide removal to enhance a hydrogen content thereof.

* * * * *